US00PP10527P

United States Patent [19]

Noack

[11] Patent Number: Plant 10,527

[45] Date of Patent: Aug. 4, 1998

[54] GROUND COVER ROSE PLANT NAMED 'FLOWER CARPET YELLOW'

[76] Inventor: Reinhard Noack, Im Fenne 54, 33334 Gütersloh, Germany

[21] Appl. No.: 783,314

[22] Filed: Jan. 15, 1997

[30] Foreign Application Priority Data

Jan. 30, 1996 [EP] European Pat. Off. ..... 186/96

[51] Int. Cl.[6] ..... A01H 5/00

[52] U.S. Cl. ..... Plt./1

[58] Field of Search ..... Plt./1, 3, 8.2, 24

*Primary Examiner*—Howard J. Locker

*Attorney, Agent, or Firm*—Burns, Doane, Swecker & Mathis, L.L.P.

[57] ABSTRACT

A new and distinct variety of ground cover rose plant is provided which forms attractive soft light yellow blossoms. The new variety exhibits a compact growth habit that renders it suitable for growing as an ornamental ground cover in the landscape. The foliage is glossy and contrasts well with the light yellow blossoms. The reproductive organs and pollen provide a darker bright yellow coloration at the center of each fully open blossom. The petals drop off cleanly as the blossoms mature. The new variety propagates well from cuttings and by budding and exhibits an excellent resistance to blackspot, mildew, and rust.

1 Drawing Sheet

SUMMARY OF THE INVENITON

Ground cover rose plants are known and are being used to advantage in an increasing number of landscape plans. However, there remains a need for additional varieties of ground cover roses with the demand being the greatest for those having highly attractive blossoms in combination with good disease resistance.

The new variety of ground cover rose plant of the present invention was created at Gütersloh, Germany by artificial pollination during May 1990 wherein two parents were crossed which previously had been studied in the hope that they would contribute the desired characteristics. The female parent (i.e., the seed parent) was the 'Immensee' variety (non-patented in the United States). The 'Immensee' variety possesses light pink to near white single blossoms. The male parent (i.e., the pollen parent) was the 'Westfalengold' variety (non-patented in the United States). The parentage of the new variety can be summarized as follows:

'Immensee'×'Westfalengold'.

The seeds resulting from the above pollination were sown and small plants were obtained which physically and biologically differ from each other. Selective study during 1991 resulted in the identification of a single plant of the new variety.

It is found that the new ground cover rose plant possesses the following combination of characteristics:

(a) forms attractive light yellow blossoms,
(b) exhibits a low, dense, and compact growth habit,
(c) forms attractive glossy foliage that contrasts well with the light yellow blossoms,
(d) exhibits excellent disease resistance with respect to blackspot, mildew, and rust, and
(e) is particularly suited for growing as attractive ornamentation in the landscape.

The new variety meets the needs of the horticultural industry and can be grown to advantage as attractive ornamentation in parks, gardens, public areas, and residential landscapes.

The new variety of the present invention from 1992 to date has been found to readily undergo asexual reproduction in Germany by the use of cuttings and by budding. Such asexual reproduction as performed in Germany has shown that the characteristics of the new variety are homogeneous and stable and are strictly transmissible from one generation to another.

The new variety has been named the 'Flower Carpet Yellow' variety. The new variety also is known as the 'Noason' variety in Europe.

BRIEF DESCRIPTION OF THE PHOTOGRAPH

The accompanying photograph shows as nearly true as it is reasonably possible to make the same in a color illustration of this character, flowers and buds of the new variety. The illustrated rose plants were photographed during July, 1993, while growing in the field at Gütersloh, Germany. Such plants were budded approximately one year earlier. A profusion of buds and blossoms in various stages of opening is illustrated. The attractive appearance of the blossoms is retained upon aging (as illustrated).

DETAILED DESCRIPTION

The chart used in the identification of the colors is that of The Royal Horticultural Society (R.H.S. Colour Chart) of London, England. Color terminology in common terms sometimes is included as an aid to the reader. The description is based on the observation of specimens of the new variety while growing outdoors during July at Gütersloh, Germany.

Class: Ground cover.

Parentage:

*Female.*—'Immensee' (non-patented in the United States).

*Male.*—'Westfalengold' (non-patented in the United States).

Plant:

*Form.*—Vigorous, compact, well covers the ground, and assumes an ideal ground cover growth habit.

*Size.*—A one year-old plant typically exhibits a height of approximately 60 cm. and a width of approximately 60 cm. A two year-old plant typically exhibits a height of approximately 80 cm. and a width of approximately 80 cm.

Branches:

*Color.*—Young stems: light green, Yellow-Green Group 144A, and with a smooth surface.

*Cane length.*—A one year-old plant typically exhibits a cane length of approximately 30 to 40 cm. A two year-old plant typically exhibits a cane length of approximately 40 to 60 cm. Adult wood: medium green slightly darker than young stems, and with a smooth surface.

*Thorns.*—Size: medium, approximately 5 mm. in length on average, and slightly curved downward. Position: irregular. Color: initially light red-brown and changing to dark brown, greyed-orange group 174A, with maturity. Quantity: average.

Leaves:

*Stipules.*—Light green in coloration.

*Leaflets.*—Number: commonly 5 or 7. Configuration: oval and pointed. Quantity: very abundant. Size: medium. Mature leaves on a one year-old plant typically have a length of approximately 2.5 to 3.5 cm. and a width of approximately 1.5 to 2 cm. Serration: slightly serrate and ordinary. Color (young foliage): Upper surface: light green, yellow-green group 144A. Under surface: slightly lighter green, yellow-green group 144B. Color (adult foliage): Upper surface: slightly darker than young foliage, green group 137B. Under surface: somewhat darker green than new foliage, green group 139C. General appearance: dense, green foliage that is glossy on the upper surface and matte on the under surface. Texture: leathery.

Inflorescence:

*Number of flowers.*—Numerous and commonly in large sprays. Commonly as many as approximately 25 to 30 blooms are present per spray.

*Peduncle.*—Near green group 141A to 141B in coloration, approximately 3 to 4 cm. in length, and somewhat soft.

*Sepals.*—Commonly extend beyond the bud and are pointed, commonly approximately 1.5 to 2 cm. in length, and near green group 135A to 135B in coloration.

*Buds.*—Shape: initially pointed (as illustrated). Length: approximately 3 cm. on average. Color when opening: light soft yellow, yellow group 6A to 6D with some reddish coloration on the edges, near greyed-red group 179A.

*Flower.*—Form: initially cup-shaped with flattening upon maturity. Appearance: satiny on both petal surfaces. Diameter: approximately 5 cm. on average. Color (when opening begins): Upper surface: predominantly yellow group 6A. Under surface: predominantly yellow group 6D. Color (when blooming): Upper surface: the bright yellow coloring of pollen and reproductive organs becomes visible at center, and attractively contrasts with the petals that are predominantly yellow group 6A. Under surface: predominantly yellow group 6D. Color (at end of opening): Upper surface: yellow coloration lightens somewhat. Under surface: yellow coloration lightens somewhat. Fragrance: light. Lasting quality: good. The individual blossoms last approximately three to four days on the plant and approximately three days when cut and placed in a vase. Petal form: broad, fan-shaped, with the outer petals commonly possessing an indented central margin. Petaloids: commonly none. Petal number: approximately 10 to 15 on average. Petal arrangement: generally arranged in a regular pattern with overlapping edges. Petal drop: good with a clean disengagement of the petals. Stamens: regularly arranged around the styles. Filaments: regularly arranged around the styles and are nearly transparent in appearance. Pollen: bright yellow in coloration. Stigmas: bright yellow-orange, orange group 24A in coloration. Styles: thin, bunched, and tend to be of substantially the same length. Hips: small, round, and green with a reddish tint.

Development:

*Vegetation.*—Strong.

*Blooming.*—In large sprays.

*Aptitude to bear fruit.*—Good.

*Winter hardiness.*—Good.

*Resistance to disease.*—Excellent with respect to blackspot, mildew, and rust.

I claim:

1. A new and distinct variety of ground cover rose plant characterized by the following combination of characteristics:

(a) forms attractive light yellow blossoms,
(b) exhibits a low, dense, and compact growth habit,
(c) forms attractive glossy foliage that contrasts well with the light yellow blossoms,
(d) exhibits excellent disease resistance with respect to blackspot, mildew, and rust, and
(e) is particularly suited for growing as attractive ornamentation in the landscape;

substantially as herein shown and described.

* * * * *

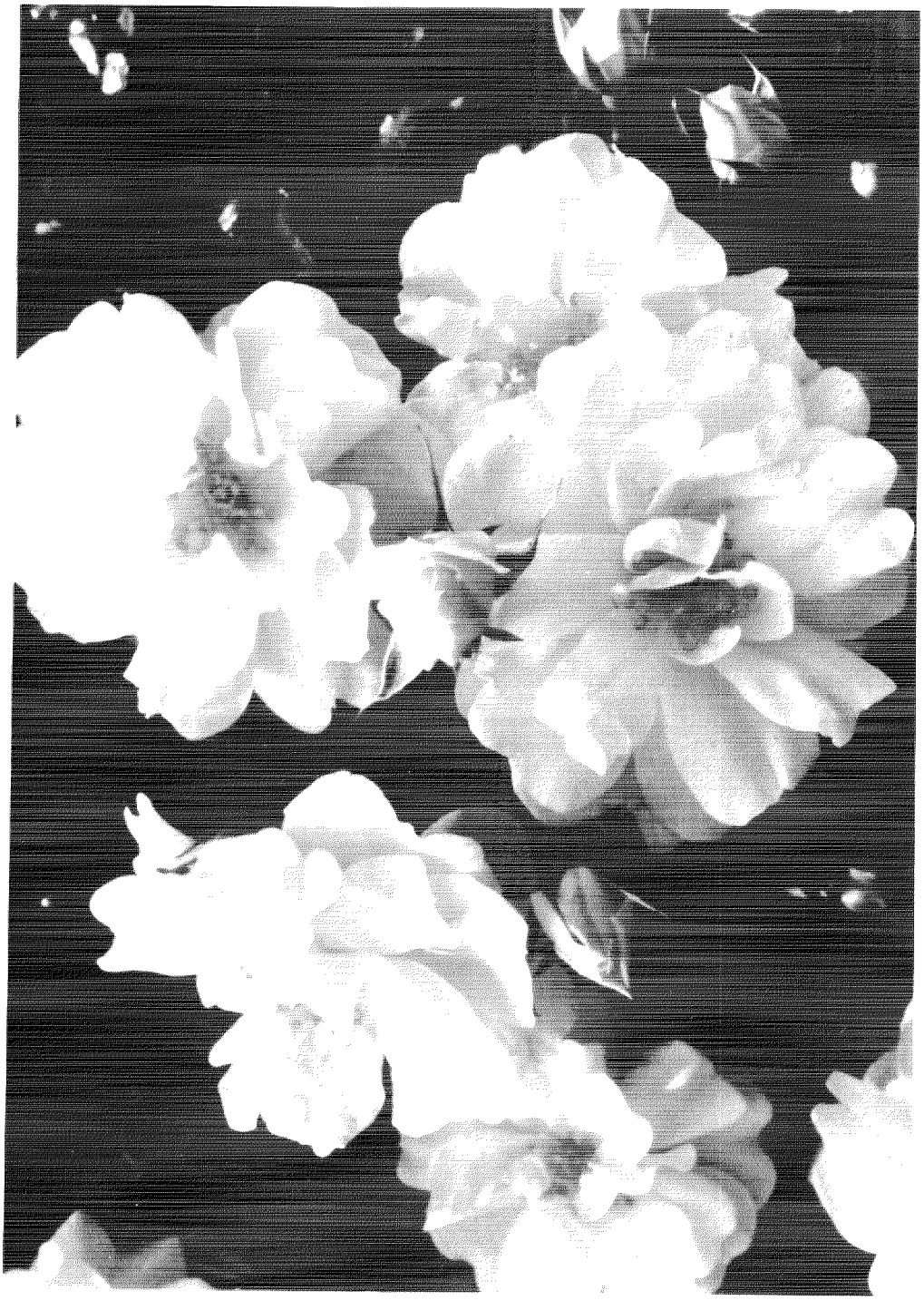

UNITED STATES PATENT AND TRADEMARK OFFICE

CERTIFICATE OF CORRECTION

PATENT NO. : PP 10,527
DATED : August 4, 1998
INVENTOR(S) : Reinhard Noack

It is certified that error appears in the above-identified patent and that said Letters Patent is hereby corrected as shown below:

Title page,
Item [54], Title, delete "FLOWER CARPET YELLOW" and insert -- 'NOASON' --.

Column 2,
Line 5, delete "'Flower Carpet Yellow'" and insert -- 'Noason' --.

Signed and Sealed this

Twenty-third Day of May, 2006

JON W. DUDAS
*Director of the United States Patent and Trademark Office*